United States Patent
Igarashi

(10) Patent No.: US 12,064,525 B2
(45) Date of Patent: Aug. 20, 2024

(54) DRY STERILIZING DEVICE AND DRY STERILIZING METHOD

(71) Applicant: USHIO DENKI KABUSHIKI KAISHA, Tokyo (JP)

(72) Inventor: Tatsushi Igarashi, Tokyo (JP)

(73) Assignee: USHIO DENKI KABUSHIKI KAISHA, Tokyo (JP)

(*) Notice: Subject to any disclaimer, the term of this patent is extended or adjusted under 35 U.S.C. 154(b) by 0 days.

(21) Appl. No.: 17/827,595

(22) Filed: May 27, 2022

(65) Prior Publication Data
US 2022/0288247 A1 Sep. 15, 2022

Related U.S. Application Data

(63) Continuation of application No. 16/390,028, filed on Apr. 22, 2019, now abandoned.

(30) Foreign Application Priority Data

Apr. 24, 2018 (JP) ................. 2018-083033

(51) Int. Cl.
*A61L 2/00* (2006.01)
*A47K 10/48* (2006.01)
*A61L 2/26* (2006.01)

(52) U.S. Cl.
CPC ............ *A61L 2/0047* (2013.01); *A47K 10/48* (2013.01); *A61L 2/26* (2013.01); *A61L 2202/11* (2013.01); *A61L 2202/14* (2013.01)

(58) Field of Classification Search
CPC ...... A61L 2/0047; A61L 2/26; A61L 2202/11; A61L 2202/14; A61L 2/022; A47K 10/48;

(Continued)

(56) References Cited

U.S. PATENT DOCUMENTS

| | | | |
|---|---|---|---|
| 7,276,059 B2 | 10/2007 | Irwin | |
| 8,253,332 B2 | 8/2012 | Yasuda et al. | |

(Continued)

FOREIGN PATENT DOCUMENTS

| | | | |
|---|---|---|---|
| JP | S63-501622 A | 6/1988 | |
| JP | H06-62981 A | 3/1994 | |

(Continued)

OTHER PUBLICATIONS

English translation of KR-200348688-Y1 (Year: 2004).*

(Continued)

*Primary Examiner* — Regina M Yoo
(74) *Attorney, Agent, or Firm* — Studebaker & Brackett PC

(57) ABSTRACT

A sterilizing device includes a housing having an opening in at least one direction thereof. The housing also has a hollow portion configured to allow insertion of an object (target) including part of a human body from the opening into the hollow portion. The sterilizing device also includes at least one air blower unit configured to send a flow of air toward an interior of the hollow portion, and at least one ultraviolet light emitting unit configured to emit ultraviolet light toward the interior of the hollow portion. The ultraviolet light emitted from each ultraviolet light emitting unit includes at least part of ultraviolet light having a wavelength between 190 nm and 230 nm and at least part of ultraviolet light having a wavelength between 230 nm and 237 nm, but does not include ultraviolet light having a wavelength below 190 nm and beyond 237 nm.

17 Claims, 9 Drawing Sheets

(58) Field of Classification Search
CPC .......... A61N 5/0624; A61N 2005/0654; A61N 2005/0661
See application file for complete search history.

(56) References Cited

U.S. PATENT DOCUMENTS

| | | | |
|---|---|---|---|
| 10,786,586 | B2 | 9/2020 | Igarashi |
| 10,910,210 | B2 | 2/2021 | Yagyu et al. |
| 2008/0199354 | A1 | 8/2008 | Gordon |
| 2009/0096343 | A1* | 4/2009 | Fujisawa ................. H01J 65/00 313/113 |
| 2009/0096376 | A1* | 4/2009 | Matsuzawa ............. H01J 61/35 313/637 |
| 2010/0266446 | A1 | 10/2010 | Constantacos |
| 2015/0265346 | A9 | 9/2015 | Randers-Pehrson et al. |
| 2016/0107000 | A1 | 4/2016 | Randers-Pehrson et al. |
| 2017/0049915 | A1* | 2/2017 | Brais .................... H05B 47/115 |
| 2018/0078101 | A1 | 3/2018 | Satermo |
| 2018/0230011 | A1 | 8/2018 | Naito et al. |
| 2018/0243582 | A1 | 8/2018 | Kaneda et al. |
| 2018/0371733 | A1 | 12/2018 | Childress et al. |
| 2019/0038914 | A1 | 2/2019 | Igarashi et al. |
| 2019/0117802 | A1 | 4/2019 | Hishinuma et al. |
| 2019/0192708 | A1 | 6/2019 | Igarashi |
| 2020/0234941 | A1 | 7/2020 | Yagyu et al. |

FOREIGN PATENT DOCUMENTS

| | | | | |
|---|---|---|---|---|
| JP | H11-76099 | A | 3/1999 | |
| JP | 2006-187396 | A | 7/2006 | |
| JP | 2009-224089 | A | 10/2009 | |
| JP | 3157460 | U | 2/2010 | |
| JP | 2011-142930 | A | 7/2011 | |
| JP | 2013-244248 | A | 12/2013 | |
| JP | 2017-136145 | A | 8/2017 | |
| KR | 200348688 | Y1 * | 5/2004 | ............. A47K 10/48 |
| WO | 87/02256 | A1 | 4/1987 | |
| WO | 2016/196904 | A1 | 12/2016 | |
| WO | WO-2017135190 | A1 * | 8/2017 | ........... A61L 2/0047 |

OTHER PUBLICATIONS

An Office Action; "Notice of Reasons for Refusal," mailed by the Japanese Patent Office on Mar. 28, 2023, which corresponds to Japanese Patent Application No. 2022-079164 and is related to U.S. Appl. No. 17/827,595; with English language translation.

An Office Action; "Notice of Reasons for Refusal", mailed by the Japanese Patent Office on Mar. 15, 2022, which corresponds to Japanese Patent Application No. 2018-083033 and is related to U.S. Appl. No. 16/390,028; with English language translation.

An Office Action; "Notice of Reasons for Refusal," mailed by the Japanese Patent Office on Aug. 22, 2023, which corresponds to Japanese Patent Application No. 2022-079164 and is related to U.S. Appl. No. 17/827,595; with English language translation.

* cited by examiner

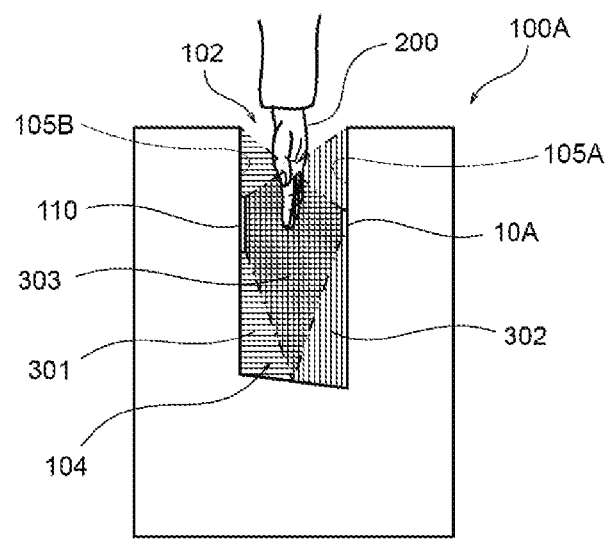
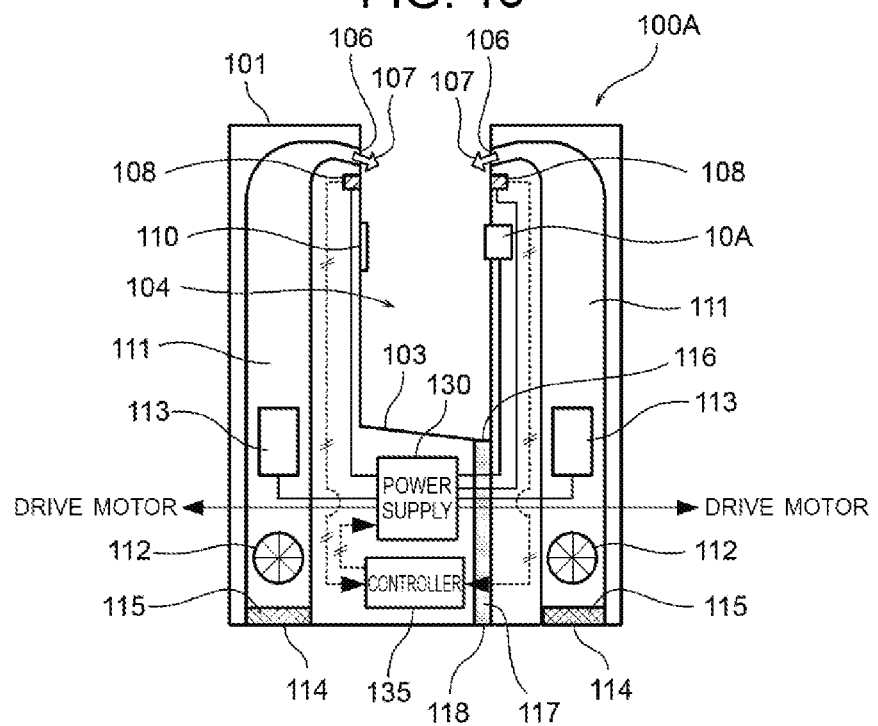

DRY STERILIZING DEVICE AND DRY STERILIZING METHOD

CROSS-REFERENCE TO RELATED APPLICATION

This application is a Continuation of U.S. patent application Ser. No. 16/390,028 filed Apr. 22, 2019, which claims priority to and the benefit of Japanese Patent Application No. 2018-083033 filed Apr. 24, 2018, the entire contents of which are incorporated herein by reference.

FIELD OF THE INVENTION

The present invention relates to a device that dries and sterilizes an object including part of a human body, such as a wet hand, and also relates to a method of drying and sterilizing an object including part of a human body, such as a wet hand.

DESCRIPTION OF THE RELATED ART

A hand dryer is used to quickly remove water droplets from wet hands and wet fingers after washing the hands. The hand dryer is a device for sending a warm current of air to the wet hands and fingers to dry the hands and fingers. Because the hand dryer is convenient, easy to install and easy to use, it has become widespread at hand-washing places in building such as business buildings, commercial facilities and schools.

On the other hand, sanitation is more important to hospitals, nursing homes and food factories, and sterilization and disinfection of bacteria are strongly required. Thus, these facilities use devices for drying and sterilizing the hands and fingers to sterilize the bacteria on the hands and fingers.

For example, Japanese Utility Model Registration No. 3157460 discloses a hand dryer (air towel) that dries and sterilizes hands after washing the hands with water. This hand dryer has an ultraviolet sterilization lamp, and applies a warm wind to the hands and fingers while irradiating the hands and fingers with the ultraviolet light at the wavelength in a range from 200 nm to 280 nm.

Japanese Patent Application Laid-Open Publication No. 2011-142930 discloses a hand dryer-sterilizer that includes a dryer for applying a warm wind to hands and an ultraviolet sterilization lamp for sterilizing the hands with the ultraviolet light. This hand dryer-sterilizer has a light shielding plate to shield the ultraviolet light, which is emitted from the ultraviolet sterilization lamp, in order to prevent the ultraviolet light from entering human's eyes.

SUMMARY OF THE INVENTION

The hand dryer of Japanese Utility Model Registration No. 3157460 does not consider adverse influences of the ultraviolet light to a human body when the hands are irradiated with the ultraviolet light. Japanese Utility Model Registration No. 3157460 teaches that the wavelength of the ultraviolet sterilization lamp is set to 253.7 nm because the ultraviolet light having such wavelength provides the strongest sterilization effect. This wavelength sterilizes bacteria such as *Escherichia coli* (O-157) and *Staphylococcus aureus* (MRSA), but can harm the human body.

The hand dryer-sterilizer of Japanese Patent Application Laid-Open Publication No. 2011-142930 does not mention the wavelength of the ultraviolet light emitted from the ultraviolet sterilization lamp, but mentions that it adversely influences the human eyes. Thus, it can be assumed that the ultraviolet light emitted from the ultraviolet sterilization lamp contains a wavelength component that hurts the human body.

Accordingly, if the technologies of Japanese Utility Model Registration No. 3157460 and Japanese Patent Application Laid-Open Publication No. 2011-142930 are used, there is a possibility that normal cells of a human body would seriously be damaged as an accumulated amount of irradiation of the ultraviolet light to the hands from the ultraviolet sterilization lamp increases. Thus, there is a serious concern to a human's health, e.g., photo-aging and skin cancer may occur when an accumulated amount of irradiation of the ultraviolet light to the hands from the ultraviolet sterilization lamp increases.

In view of these facts and concerns, an object of the present invention is to provide a dry sterilizing device that dries and sterilizes an object including part of a human body without adversely influencing the human body. Another object of the present invention is to provide a dry sterilizing method that dries and sterilizes an object including part of a human body without adversely influencing the human body.

In order to achieve these objects, one aspect of the present invention provides a sterilizing device that includes a housing having an opening in at least one direction thereof, and also having a hollow portion configured to allow insertion of an object (target) including part of a human body from the opening into the hollow portion. It may be said that the opening is part of the hollow portion. The sterilizing device also includes at least one air blower unit configured to make a flow of air toward an interior of the hollow portion, and at least one ultraviolet light emitting unit configured to emit ultraviolet light toward the interior of the hollow portion. The ultraviolet light emitted from the ultraviolet light emitting unit(s) includes at least part of a wavelength between 190 nm and 230 nm and at least part of a wavelength between 230 nm and 237 nm, but does not include a wavelength below 190 nm and beyond 237 nm.

With the ultraviolet light in the above-mentioned wavelength range, it is possible to deactivate the target (bacteria) on the human body while avoiding or reducing the harmful effect on the human cells. Thus, the dry sterilizing device can dry and sterilize the target including part of the human body, without adversely influencing the human body.

Each of the ultraviolet light emitting units may include a light source to emit light including ultraviolet light having a wavelength between 190 nm and 237 nm, and a filtering member through which the light emitted from the light source passes, such that the light having passed through the filtering member proceeds toward the interior of the hollow portion. When the light emitted from the light source enters the filtering member at an incident angle of zero degree, the filtering member may transmit at least part of the ultraviolet light having the wavelength between 190 nm and 230 nm and at least part of the ultraviolet light having the wavelength between 230 nm and 237 nm and to block transmission of the ultraviolet light having the wavelength outside a wavelength range between 190 nm and 237 nm.

When the filtering member having the above-described optical characteristics is used, it is possible to utilize the light emitted from the light source at a high efficiency, and can save the energy to be spent in the dry sterilizing device. Also, the filtering member having the above-described optical characteristics can transmit the light entering at a large incident angle. Thus, it is possible to allow the light having a large diffusion angle to exit from the filtering member and provide a large effective irradiation area.

The light source of the sterilizing device may be a KrCl excimer lamp or a KrBr excimer lamp.

With such light source, the light emitted from the light source can have a center wavelength between 190 nm and 230 nm. When the light source is the KrCl excimer lamp, the center wavelength of the emitted light is 222 nm. When the light source is the KrBr excimer lamp, the center wavelength of the emitted light is 207 nm.

A lighting tube of the KrCl excimer lamp or the KrBr excimer lamp of the sterilizing device may be made from a dielectric substance, and may be a rectangular parallelepiped hollow tube having a rectangular cross-sectional shape. When the light source has a rectangular parallelepiped shape, it is possible to place the entire light emitting surface of the excimer lamp in the vicinity of the filtering member. Thus, it is possible to make the ultraviolet light emitting unit compact.

The ultraviolet light emitting unit of the sterilizing unit may include a reflection member configured to reflect the light emitted from the light source toward the interior of the hollow portion through the filtering member. With this configuration, it is possible to efficiently (effectively) utilize the light emitted from the light source.

The filtering member of the sterilizing device may have a dielectric multi-layer film made from at least one $SiO_2$ layer and at least one $Al_2O_3$ layer. Alternatively, the filtering member of the sterilizing device may have a dielectric multi-layer film made from at least one $HfO_2$ layer and at least one $SiO_2$ layer.

Such configuration can appropriately provide the above-described optical characteristics. When the filtering member of the sterilizing device has the dielectric multi-layer film made from the $HfO_2$ layer(s) and the $SiO_2$ layer(s), it is possible to reduce the number of the layers included in the dielectric multi-layer film, as compared to the filtering member having the dielectric multi-layer film made from the $SiO_2$ layer(s) and the $Al_2O_3$ layer(s). When the filtering member of the sterilizing device has the dielectric multi-layer film made from the $HfO_2$ layer(s) and the $SiO_2$ layer(s), therefore, it is possible to obtain a high transmittance for the ultraviolet light having a peak wavelength among the light emitted from the light source. In addition, because the number of the layers included in the dielectric multi-layer film is small (or decreased), it is possible to manufacture the filtering member at a low(er) cost while having a good reproducibility with regard to the cutoff wavelength.

The ultraviolet light emitting unit of the sterilizing device may emit the ultraviolet light such that the ultraviolet light reaches at least part of an inner wall of the hollow portion. With such configuration, it is possible to sterilize bacteria adhering on the inner wall of the hollow portion, and prevent the bacteria from flying to the environment (atmosphere) with the wind.

The opening of the hollow portion of the sterilizing device may be provided at an upper portion of the hollow portion, and the hollow portion may have at least two facing side walls and a bottom opposite to the opening. The ultraviolet light emitting unit may emit the ultraviolet light such that the ultraviolet light reaches the side walls and the bottom of the hollow portion. With such configuration, it is possible to appropriately sterilize the bacteria adhering on the inner wall of the hollow portion. It is also possible to appropriately irradiate the entire surface of the object with the ultraviolet light when the object is inserted into the hollow portion. Thus, it is possible to appropriately sterilize the bacteria adhering on the surface of the object.

The hollow portion of the housing of the sterilizing device may have two facing side walls, and the two ultraviolet light emitting units may be disposed on the two side walls, respectively. With this configuration, the object is irradiated with the ultraviolet light coming from the two directions when the object is inserted into the hollow portion.

The above-mentioned "at least one ultraviolet light emitting unit" of the sterilizing device may be a single ultraviolet light emitting unit. The hollow portion of the housing may have two facing side walls, the single ultraviolet light emitting unit may be disposed on one of the two side walls, and a reflection mirror may be disposed on the other of the two side walls such that the reflection mirror reflects part of the ultraviolet light emitted from the single ultraviolet light emitting unit toward the interior of the hollow portion. With this configuration, only the single ultraviolet light emitting unit is used, but it is still possible to irradiate the object with the ultraviolet light from a plurality of directions. Thus, it is possible to save the energy spent by the sterilizing device.

The sterilizing device may further include at least one sensor unit, a power supply unit, and a controller unit. The sensor unit(s) may be configured to detect presence and/or absence of the object in the hollow portion. The power supply unit may be configured to supply electricity to the air blower unit(s), the ultraviolet light emitting unit(s) and the sensor unit(s). The controller unit may be configured to control the power supply unit based on a detection result of the sensor unit(s), in order to control operations of the air blower unit(s) and the ultraviolet light emitting unit(s). With such configuration, the controller unit can activate and deactivate the respective components of the sterilizing device at appropriate timing.

The controller unit of the sterilizing device may control the power supply unit after a predetermined period of time elapses upon detecting absence of the object in the hollow portion by the sensor unit(s), to deactivate the air blower unit(s) and the ultraviolet light emitting unit(s).

In other words, the controller may continue the activation of the air blower unit(s) and the ultraviolet light emitting unit(s) for a predetermine period of time even after the object (target) leaves the hollow portion. With such configuration, the air blows for a predetermined period of time after the target is no longer present in the hollow portion. This facilitates (accelerates) the movement of the water droplets toward a water receiving portion of the dry sterilizing device from the inner wall of the hollow portion. Also, the ultraviolet light is emitted for a predetermined period of time after the target is no longer present in the hollow portion. This sterilizes the bacteria remaining in the hollow portion.

When the sensor unit(s) of the sterilizing device detects the presence of the object in the hollow portion, the controller unit may control the power supply unit to activate the ultraviolet light emitting unit(s). The controller unit may control the power supply unit to activate the air blower unit(s) after a predetermined period of time elapses upon activation of the ultraviolet light emitting unit(s).

When the emission of the ultraviolet light starts upon detecting the target in the hollow portion but prior to the blowing of the air, the sterilization of the bacteria on the target is firstly carried out with the ultraviolet light, and then the removal of the water droplets from the target is carried out with the wind (air). Thus, it is possible to reduce the bacteria contained in the water droplets that flies (scatters)

with the wind blowing from the air nozzles. This suppresses the diffusion of the bacteria in the hollow portion and into the atmosphere.

The controller unit may control the power supply unit for a predetermined period of time to activate the ultraviolet light emitting unit(s) while the sensor unit(s) is not detecting the presence of the object in the hollow portion. With such configuration, it is possible to sterilize the bacteria remaining in the hollow portion and suppress the growth and increase of the bacteria in the hollow portion.

The controller unit may control operations of the ultraviolet light emitting unit(s) such that an activation period of the ultraviolet light emitting unit(s) and a deactivation period of the ultraviolet light emitting unit(s) are alternately repeated for a predetermined number of times while the sensor unit(s) is not detecting the presence of the object in the hollow portion. By periodically carrying out the emission of the ultraviolet light, it is possible to sterilize the bacteria in the hollow portion in a more appropriate manner.

The controller unit may keep deactivating the ultraviolet light emitting unit(s) if the sensor unit(s) does not detect the presence of the object in the hollow portion for a predetermined period of time after deactivation of the ultraviolet light emitting unit(s) upon detecting the absence of the object in the hollow portion by the sensor unit(s).

With such configuration, the sterilization to the interior of the hollow portion is not carried out by the ultraviolet light while there is a possibility that a next user will come. This ensures that the blowing of the air and the emission of the ultraviolet light to the next user is appropriately carried out.

According to another aspect of the present invention, there is provided a dry sterilizing method including a step of making a flow of air toward an interior of a hollow portion of a housing of a sterilizing device. The hollow portion has an opening toward at least one direction of the housing to allow insertion of an object including part of a human body from the opening into the hollow portion. The method also includes a step of irradiating the interior of the hollow portion with ultraviolet light. The ultraviolet light includes at least part of a wavelength between 190 nm and 230 nm and at least part of a wavelength between 230 nm and 237 nm, but does not include a wavelength below 190 nm and beyond 237 nm.

The ultraviolet light having the above-mentioned wavelength range can deactivates the bacteria on the human body (target) while avoiding or suppressing the harmful effect on the human cells. Therefore, this sterilizing method can dry and sterilize the target including part of the human body, without adversely influencing the human body.

According to the present invention, the sterilizing device has a unit for emitting ultraviolet light having the wavelength between 190 nm and 230 nm and between 230 nm and 237 nm, but not including ultraviolet light having a wavelength below 190 nm and beyond 237 nm. Thus, it is possible to dry and sterilize the object including part of the human body without adversely influencing the human body.

BRIEF DESCRIPTION OF THE DRAWINGS

FIG. 12 is similar to FIG. 2, and shows a side view to show another example of a dry sterilizing device.

FIG. 13 is similar to FIG. 4, and illustrates a cross-sectional view of the dry sterilizing device shown in FIG. 12.

DETAILED DESCRIPTION OF THE INVENTION

Embodiments of the present invention will now be described in detail with reference to the accompanying drawings.

General Structure of a Dry Sterilizing Device

Figure 1:
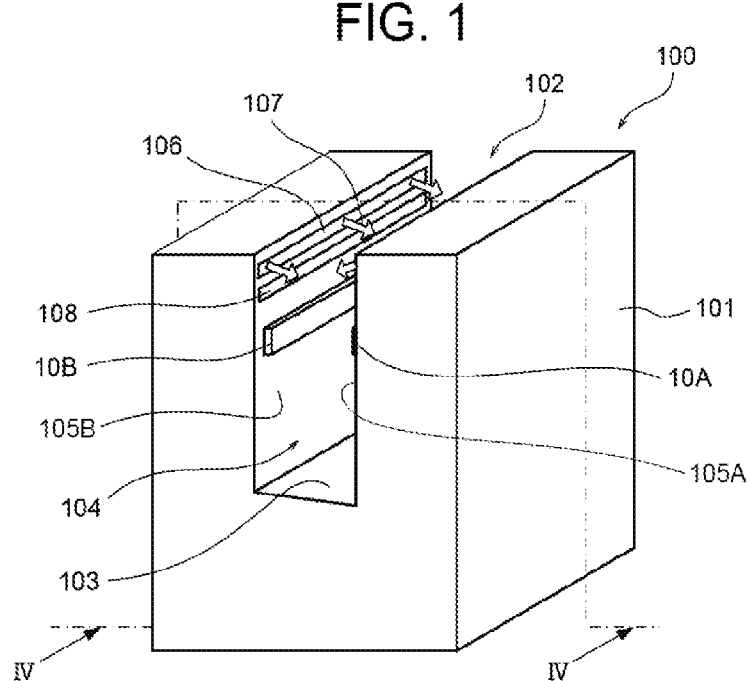
FIG. 1 is a perspective view that shows an exemplary structure of a dry sterilizing device according to an embodiment of the present invention.
Figure 2:
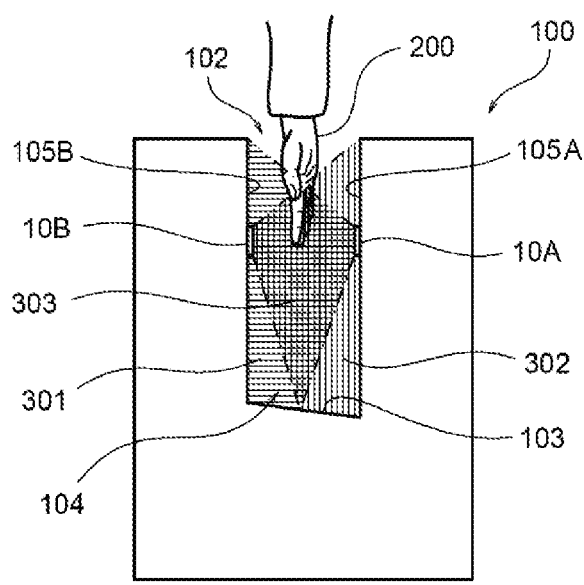
FIG. 2 is a side view of the dry sterilizing device shown in FIG. 1.

FIG. 1 is a perspective view that shows an exemplary structure of a dry sterilizing device 100 according to an embodiment of the present invention. FIG. 2 is a side view of the dry sterilizing device 100.

The dry sterilizing device 100 of this embodiment is a device for drying and sterilizing wet hands and fingers of a human when he/she washes hands and fingers with water. The dry sterilizing device 100 may be installed at handwashing places in facilities such as hospitals, nursing homes and food factories. These facilities demand good sanitation.

As shown in FIG. 1, the dry sterilizing device 100 has a housing 101. The housing 101 has an opening 102 at its upper portion. The opening 102 opens upward. The housing 101 has an inner bottom 103 at its lower part. The inner bottom 103 is opposite to the opening 102. Below the opening 102, defined is a hollow portion 104. The lower end of the hollow portion 104 is the inner bottom 103. As shown in FIG. 2, a user's wet hand and fingers 200 are dried and sterilized as the hand and fingers 200 enter the hollow portion 104 from the opening 102. The width of the hollow portion 104 has a size that allows the two hands and ten fingers 200 of the user to enter the hollow portion 104.

Air nozzles 106 are disposed at two opposite side walls 105A and 105B of the hollow portion 104, respectively. The air nozzles 106 supply (inject) a warm wind 107 toward the interior of the hollow space 104 in order to dry the hands and fingers, which are wet after the user washes the hands and fingers with water. Each of the air nozzles 106 has a rectangular shape, for example, as shown in FIG. 1. A warm wind 107 blows, in the form of sheet, from each of the air nozzles 106.

A sensor 108 is disposed below each of the air nozzles 106 to detect (determine) whether a user's hands and fingers are present in the hollow space 104.

Ultraviolet light emitting units 10A and 10B are disposed below the sensors 108, respectively, to emit ultraviolet light to the interior of the hollow space 104 so as to sterilize bacteria on the user's hands and fingers.

As shown in FIG. 2, the position of the ultraviolet light emitting unit 10A, which is disposed on the side wall 105A, is decided such that the ultraviolet light emitted from the unit 10A reaches the entire opposite side wall 105B and part of the bottom 103. Likewise, the position of the ultraviolet light emitting unit 10B, which is disposed on the side wall 105B, is decided such that the ultraviolet light emitted from the unit 10B reaches the entire opposite side wall 105A and part of the bottom 103. The two ultraviolet light emitting units 10A and 10B are arranged such that the entire two side walls 105A and 105B and the entire bottom 103 of the hollow portion 104 are irradiated with the ultraviolet light emitted from the two ultraviolet light emitting units 10A and 10B.

In FIG. 2, an irradiation area 301 is an area irradiated with the ultraviolet light emitted from the ultraviolet light emitting unit 10A, and an irradiation area 302 is an area irradiated with the ultraviolet light emitted from the ultraviolet light emitting unit 10B. An irradiation area 303 is an area where the areas 301 and 302 overlap.

Therefore, the entire surface of the user's hands and fingers 200 is irradiated with the ultraviolet light as the user's hands are placed into the hollow portion 104 to cause the warm air 107 to blow from the air nozzles 106 to the entire surface of the user's hands and fingers 200 in order to dry the user's hands and fingers 200.

The ultraviolet light emitting units 10A and 10B emit ultraviolet light that includes at least part of the wavelength from 190 nm to 230 nm, and at least part of the wavelength from 230 nm to 237 nm, but does not include the wavelength below 190 nm and over 237 nm. The wavelength of the ultraviolet light emitted from the ultraviolet light emitting units 10A and 10B does not include "the wavelength outside the wavelength range from 190 nm to 237 nm." This means that the intensity of the ultraviolet light outside the wavelength range between 190 nm and 237 nm is no greater than $1/1000$ of the peak intensity of the light at the wavelength of 222 nm.

The intensive studies of the inventor found that the ultraviolet light in the wavelength range between 190 nm and 237 nm can substantially avoid the harmful effect to the human cells while deactivating (e.g., sterilizing) an object (or objects) to be sterilized, which is present at a target portion of a human body. Thus, the ultraviolet light emitted from the ultraviolet light emitting units 10A and 10B in the above-mentioned wavelength range does not exert the harmful effect to the human body but can appropriately sterilize the bacteria on the surface of the human's hands and fingers.

As shown in FIG. 2, the bottom 103 of the hollow portion 104 inclines relative to the horizontal plane. It should be noted that although the bottom 103 inclines downward toward the side wall 105A in FIGS. 1 and 2, the inclination of the bottom 103 is not limited to the illustrated inclination (i.e., the bottom 103 may incline downward toward the side wall 105B). The bottom 103 functions as a water receiving portion to receive the water (droplets) spreading from the user's hands and fingers. The bottom 103 may have an arbitrary shape as long as the water droplets flying from the user's hands and fingers are ultimately guided to a drain 116 (FIG. 4) of the bottom 103 (will be described later).

Figure 3A:
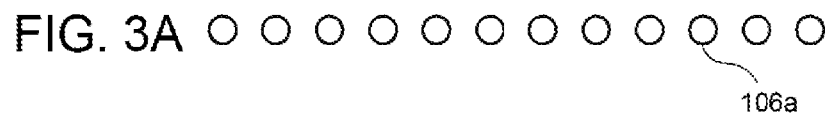
FIG. 3A shows another example of an air nozzle.
Figure 3B:
FIG. 3B shows still another example of the air nozzle.

It should be noted that although the shape of each of the air nozzles 106 is rectangular in FIG. 1, the shape of the air nozzles 106 is not limited to the rectangle. For example, as shown in FIG. 3A, a plurality of circular holes 106a may be arranged linearly across the width of the hollow portion 104. Alternatively, a plurality of circular holes 106a may be arranged in an arc, as shown in FIG. 3B.

Structure for Supplying a Warm Air

Figure 4:
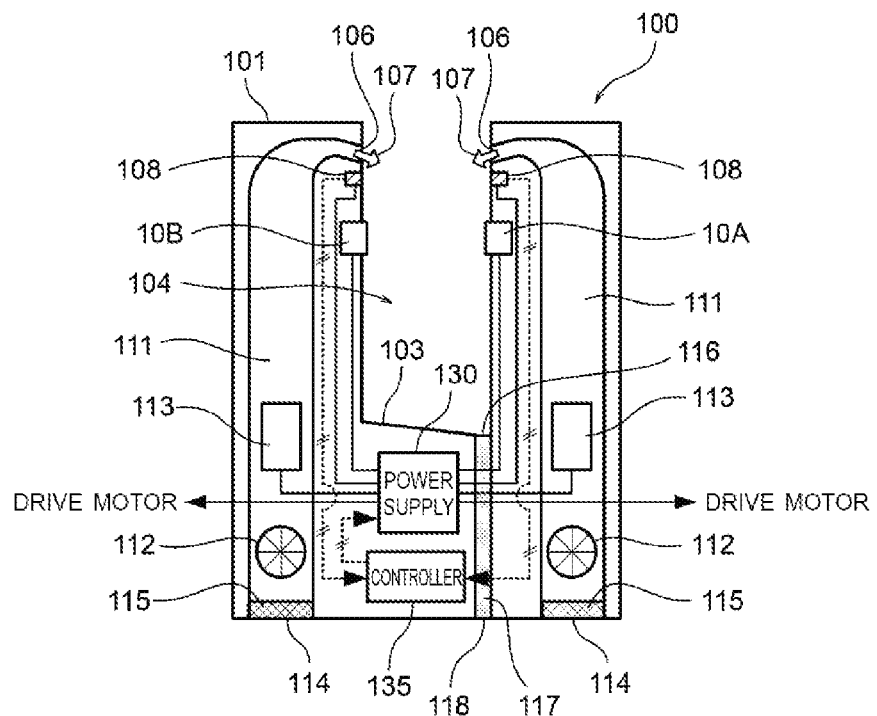
FIG. 4 is a cross-sectional view of the dry sterilizing device, taken along the line IV-IV in FIG. 1.

FIG. 4 is a cross-sectional view taken along the line IV-IV in FIG. 1. As illustrated in FIG. 4, air passages 111 are provided in the housing 101 such that the air passages 111 communicate with the air nozzles 106, respectively. In each of the air passages 111, there is provided a blower fan (air blower) 112. A heater 113 is disposed between each of the blower fans 112 and the associated air nozzle 106. Each of the blower fans 112 is rotated (driven) by an associated drive motor (not shown). As the blower fans 112 rotate, the flows of air are introduced into the respective air passages 111 from air inlets 114, which are provided at the bottom of the housing 101. Then, the high-speed air is released (sprayed) toward the interior of the hollow portion 104 from the air nozzles 106. At the same time, the heaters 113 in the air passages 111 are activated to heat the air entering from the air inlets 114. Thus, the air sprayed from the air nozzles 106 becomes the warm air 107.

It should be noted that dust filters 115 may be provided at the air inlets 114 to prevent undesired substances such as dusts in the atmosphere from entering the air passages 111.

The air passages 11, the air blowers 112, the heaters 113, the air inlets 114, the dust filters 115 and the air nozzles 106 in FIG. 4 serve in combination as the air blowing unit(s) to discharge the air to the interior of the hollow portion 104.

A power supply unit 130 supplies an electric power to the ultraviolet light emitting units 10A and 10B, the sensors 108, the heaters 113, and the drive motors of the air blowers 112. A controller 135 controls the power supply unit 130.

The sensors 108 detect presence/absence of hands and fingers in the hollow portion 104. Upon detecting the hands and fingers in the hollow portion 104, the sensors 108 send detection signals, which are indicative of presence of the hands and fingers, to the controller 135.

Based on the detection signals from the sensors 108, the controller 135 controls the ultraviolet light emitting units 10A and 10B, the heaters 113, and the drive motors of the blower fans 112. Specifically, the controller 135 controls the power supply unit 130 upon receiving the detection signals from the sensors 108, in order to start the activation of the drive motors of the blower fans 112 and the ultraviolet light emitting units 10A and 10B.

Thus, as the user inserts the hands and fingers into the hollow portion 104 of the sterilizing device 100, the high-speed warm air 107 blows from the air nozzles 106. Also, at least part of the ultraviolet light in the wavelength range between 190 nm and 230 nm and at least part of the ultraviolet light in the wavelength range between 230 nm and 237 nm are emitted to the hollow portion 104 from the ultraviolet light emitting units 10A and 10B.

The high-speed warm air 107 released (injected) from the air nozzles 106 hit and dry the wet hands and fingers in the hollow portion 104. The water droplets flying from the hands and fingers upon the air injection reach the bottom 103, which serves as the water receiving part of the hollow portion 104. Thus, the water droplets flying from the hands and fingers directly drop to the bottom 103 and/or flow downward to the bottom 103, due to the gravity, after adhering onto the side walls 105A and 105B of the hollow portion 104.

As described above, the bottom 103 inclines downward, and the downward end of the bottom 103 has the drain 116. The water droplets collected at the bottom 103 flow into the drain 116. The water droplets are guided to a drain outlet 118 from the drain 116 through a drain passage 117, and are discharged out of the device 100 from the drain outlet 118. The discharged water is then subjected to a predetermined treatment.

It should be noted that the controller 135 may keep activating the drive motors of the blower fans 112 for a predetermined period of time after the receiving of the detection signals from the sensors 108 interrupts or stops.

The controller 135 may control the temperature of each of the heaters 113. For example, when the surrounding temperature or the atmosphere temperature is high (e.g., during summer), the controller 135 may set a lower temperature to the heaters 113 or may stop the feeding of the electricity to the heaters 113.

Ultraviolet Light Emitting Unit
General Structure

Figure 5:
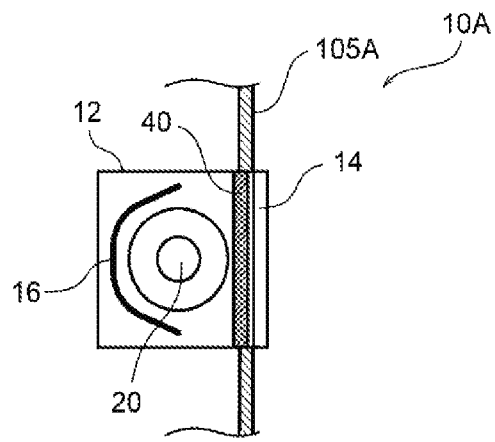
FIG. 5 shows an exemplary structure of an ultraviolet light emitting unit.

FIG. 5 shows an exemplary structure of the ultraviolet light emitting unit 10A. Because the ultraviolet light emitting unit 10B is similar to the ultraviolet light emitting unit 10A in terms of structure, the following description only describes the structure of the ultraviolet light emitting unit 10A.

The ultraviolet light emitting unit 10A has an ultraviolet lamp 20, as its light source, to emit the ultraviolet light. The ultraviolet lamp 20 is housed in a lamp chamber 12 that has, for example, a rectangular parallelepiped shape. The lamp chamber 12 has a rectangular window member 14 in its right face. The window member 14 is a plate member and made from, for example, synthetic silica glass (quartz glass). The window member 14 transmits the ultraviolet light. Behind the ultraviolet lamp 20 in the lamp chamber 12, provided is a reflection member (reflection mirror) 16 to reflect the light emitted from the ultraviolet lamp 20 toward the window member 14. The reflection member 16 has a U-shape in its cross-section, and surrounds the ultraviolet lamp 20.

The ultraviolet lamp 20 may emit the light whose center wavelength is between 190 nm and 230 nm. For example, the ultraviolet lamp 20 may be a KrBr excimer lamp that emits light with its center wavelength being 207 nm, or a KrCl excimer lamp that emits light with its center wavelength being 222 nm.

A rectangular filtering member 40 is disposed between the ultraviolet lamp 20 and the window member 14 in the lamp chamber 12. The filtering member 40 is a plate member and faces the window member 14. The filtering member 40 is an optical filter to extract the ultraviolet light that has a desired (predetermined) wavelength. The desired (predetermined) wavelength is between 190 nm and 237 nm. Specifically, the filtering member 40 transmits at least part of the ultraviolet light having the wavelength between 190 nm and 230 nm and at least part of the ultraviolet light having the wavelength between 230 nm and 237 nm. The filtering member 40 hinders (blocks) the transmission of the ultraviolet light having the wavelength outside the wavelength range between 190 nm and 237 nm.

The sentence "the filtering member 40 hinders (blocks) the transmission of the ultraviolet light" means that when the ultraviolet light emitted from the light source passes through the filtering member 40, the intensity of the ultraviolet light having the wavelength outside the wavelength range between 190 nm and 237 nm becomes $\frac{1}{1000}$ (or less) of the peak intensity of the light having the wavelength of 222 nm.

Thus, the ultraviolet light emitted from the ultraviolet lamp 20 directly enters the filtering member 40 or enters the filtering member 40 after being reflected by the reflection member 16. Then, the ultraviolet light having the wavelength outside the wavelength range between 190 nm and 237 nm is blocked by the filtering member 40. The ultraviolet light, which has passed through the filtering member 40, has the wavelength between 190 nm and 237 nm and is directed to the interior of the hollow portion 104 from the window member 14.

It should be noted that the window member 14 may protrude into the hollow portion 104 from the side wall 105A, as shown in FIG. 5. Alternatively, the surface of the side wall 105A may substantially be planar to the surface of the window member 14. If the window member 14 protrudes into the hollow portion 104, an amount of the protrusion may be decided such that the window member 14 would not significantly reduce the space available for the user's hands and fingers in the hollow portion 104.

Because the oxygen in the atmosphere absorbs the light having the wavelength below 200 nm, the interior of the lamp chamber 12 may be purged with an inert gas such as a nitrogen (N2) gas if necessary, in order to avoid that the intensity of the light emitted from the ultraviolet lamp 20 attenuates.

In this case, the window member 14 is assembled to the lamp chamber 12 such that the window member 14 becomes air-tight to the lamp chamber 12, and therefore the air does not enter the lamp chamber 12 from the hollow portion 104. Because the window member 14 can also prevent the wet air (moisture) from entering the lamp chamber 12 from the hollow portion 104, the air tightness between the window member 14 and the lamp chamber 12 protects the ultraviolet lamp 20. Furthermore, the window member 14 prevents that the filtering member 40 be contaminated (become dirty) by the flying water droplets or the like.

Ultraviolet Lamp Exemplary Structure 1

As described above, the ultraviolet lamp 20 may be a KrBr excimer lamp that emits light having the center wavelength at 207 nm, or a KrCl excimer lamp that emits light having the center wavelength at 222 nm.

Figure 6:
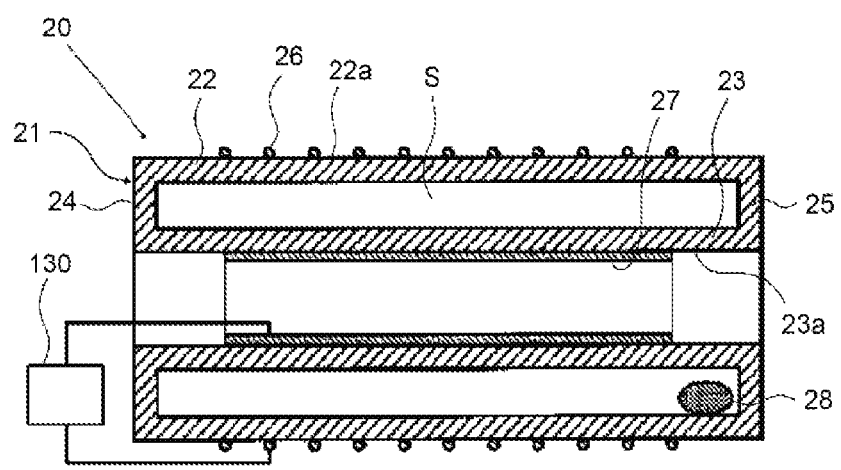
FIG. 6 is a cross-sectional view useful to describe an exemplary structure of an excimer lamp.

FIG. 6 is a cross-sectional view useful to describe an exemplary structure of the ultraviolet lamp (excimer lamp) 20. The excimer lamp 20 has a closed-type discharge vessel 21. The discharge vessel 21 has a cylindrical wall 22 and another cylindrical wall 23 (double wall structure). Each of the cylindrical walls 22 and 23 is made from a dielectric substance. The inner cylindrical wall 23 is coaxial to the outer cylindrical wall 22. The outer diameter of the cylindrical wall 23 is smaller than the inner diameter of the cylindrical wall 22. In this discharge vessel 21, the cylindrical walls 22 and 23 are connected to each other at their left ends by a sealing wall 24, and connected to each other at the other ends (right ends) by another sealing wall 25. The discharge space S is defined by the two wall members 22 and 23. The discharge space S has a cylindrical shape. The dielectric substance used to make the discharge vessel 21 is, for example, quartz glass.

A net-like electrode 26, which is made from an electrically conductive material, is disposed on (or in the vicinity of) the outer surface 22a of the cylindrical wall 22 of the discharge vessel 21. The electrode 26 may be a wire netting. A film-like electrode 27 is disposed over the outer surface 23a of the cylindrical wall 23 of the discharge vessel 21. The electrode 27 may be an aluminum film. The electrodes 26 and 27 are connected to the power supply unit 130, respectively.

A discharge gas, i.e., a mixture of krypton (Kr) and chlorine (Cl2) or bromine (Br2), has been loaded into the discharge vessel 21. A substance 28 for feeding elements, which are used for light emission, is placed in the discharge vessel 21. The substance 28 is a metal chloride or a metal bromide.

When a high-frequency voltage is applied across the two electrodes 26 and 27 of the excimer lamp 20 from the power supply unit 130, dielectric barrier discharge takes place in the discharge space S in the discharge vessel 21. As a result, an excimer is produced from the krypton element and the chlorine element (or bromine element) in the discharge vessel 21. The excimer light emitted from the excimer is radiated (released) to the outside from the mesh of the net-like electrode 26 through the wall 22.

If the excimer lamp 20 is the KrCl excimer lamp, the excimer light emitted from the excimer lamp 20 has a center wavelength at, for example, 222 nm, and includes light having the wavelength between 230 nm and 300 nm.

If the excimer lamp 20 is the KrBr excimer lamp, the excimer light emitted from the excimer lamp 20 has a center wavelength at, for example, 207 nm, and includes light having the wavelength between 230 nm and 300 nm.

In this embodiment, when the light emitted from the light source, i.e., the excimer lamp 20, enters the filtering member 40 at the incident angle of zero degree, the filtering member 40 transmits at least part of the ultraviolet light having the wavelength between 190 nm and 230 nm and at least part of the ultraviolet light having the wavelength between 230 nm and 237 nm while blocking the transmission of the ultraviolet light having the wavelength outside the wavelength range between 190 nm and 237 nm.

The filtering member 40 may have a dielectric multi-layer film, which is made from $SiO_2$ film(s) and $Al_2O_3$ film(s), or a dielectric multi-layer film, which is made from $HfO_2$ film(s) and $SiO_2$ film(s).

Ultraviolet Lamp Exemplary Structure 2

The excimer lamp 20 shown in FIGS. 5 and 6 is a tubular lamp that has a circular cross-section. The excimer lamp 20 extends in generally parallel to the longitudinal direction of the opening 102 of the hollow portion 104 of the housing 101. It should be noted, however, that the structure of the discharge vessel of the excimer lamp is not limited to a double wall (double tube) structure that has a circular cross-section. For example, the discharge vessel may be a tubular structure having a rectangular cross-section.

Figure 7A:
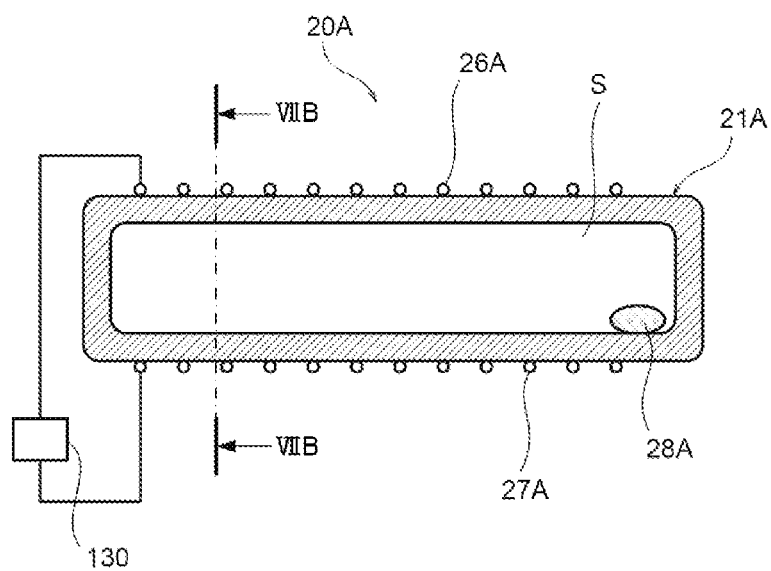
FIG. 7A is a cross-sectional view useful to describe another exemplary structure of the excimer lamp.
Figure 7B:
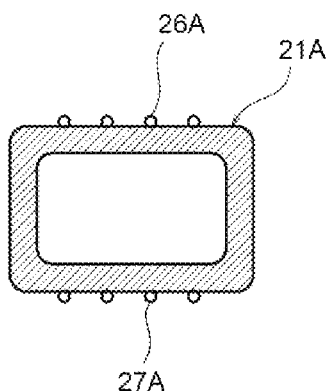
FIG. 7B is a cross-sectional view taken along the line VIIB-VIIB in FIG. 7A.

FIG. 7A is a cross-sectional view of an excimer lamp 20A that includes a discharge vessel 21A having a tubular structure. The cross-section of the discharge vessel 21A is rectangular. FIG. 7B is a cross-sectional view in the longitudinal direction. FIG. 7B is a cross-sectional view taken along the line VIIB-VIIB in FIG. 7A.

As shown in FIGS. 7A and 7B, the excimer lamp 20A includes the discharge vessel 21A that has a hollow rectangular parallelepiped shape, and is made from a dielectric substance. The dielectric substance of the discharge vessel 21A may be quartz glass.

A net-like electrode 26A, which is made from an electrically conductive material, is disposed on (or in the vicinity) the upper outer surface of the discharge vessel 21A. The electrode 26A may be a wire netting. Likewise, a net-like electrode 27A, which is made from an electrically conductive material, is disposed on (or in the vicinity) the opposite outer surface (i.e., the lower outer surface) of the discharge vessel 21A. The electrode 27A may be a wire netting. The electrodes 26A and 27A are connected to the power supply unit 130, respectively.

It should be noted that the electrodes 26A and 27A are not limited to the net-like electrodes. For example, mesh patterns, which will serve as the electrodes 26A and 27A, may be printed on the upper and lower outer surfaces of the discharge vessel 21A. Each of the mesh patterns may be made from an electrically conductive material.

A discharge gas, i.e., a mixture of krypton (Kr) and chlorine (Cl2) or bromine (Br2), has been loaded into the discharge vessel 21A. A substance 28A for feeding elements, which are used for light emission, is placed in the discharge vessel 21A. The substance 28A is a metal chloride or a metal bromide.

When a high-frequency voltage is applied across the two electrodes 26A and 27A of the excimer lamp 20A from the power supply unit 130, dielectric barrier discharge takes place in the discharge space S in the discharge vessel 21A. As a result, an excimer is produced from the krypton element and the chlorine element (or bromine element) in the discharge vessel 21A. The excimer light emitted from the excimer is radiated (released) to the outside from the mesh of the electrode 26A through the upper wall.

As mentioned earlier, the excimer lamp 20A is a tubular lamp that has a rectangular cross-section. The excimer lamp 20A can extend (can be elongated) in generally parallel to the longitudinal direction of the opening 102 of the hollow portion 104 of the housing 101.

Figure 8:
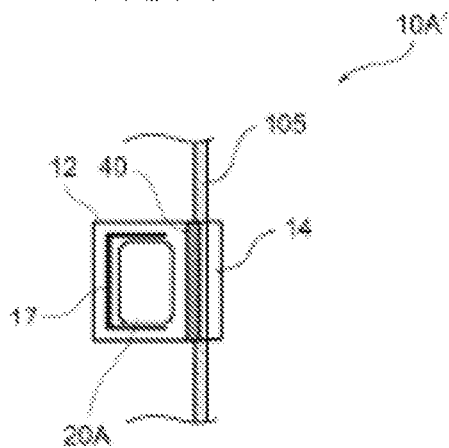
FIG. 8 is similar to FIG. 5, and illustrates another example of the ultraviolet light emitting unit.

FIG. 8 shows an exemplary structure of the ultraviolet light emitting unit 10A' when the excimer lamp 20A is used as the ultraviolet lamp. In FIG. 8 and FIG. 5, similar parts and components of the ultraviolet light emitting unit (10A', 10A) are given similar reference numerals. The similar parts and components may not be described in detail.

Because the excimer lamp 20A has a rectangular parallelepiped shape, it is possible to place the entire surface of one of the light emitting surfaces (the surface having the electrode 26A) of the excimer lamp 20A in the vicinity of the filtering member 40. Also, it is possible to place the entire surface of the other light emitting surface (the surface having the electrode 27A) of the excimer lamp 20A in the vicinity of the reflection member 17. The reflection member 17 can have a rectangular shape that conforms to the cross-sectional shape of the excimer lamp 20A. Thus, it is possible to make the ultraviolet light emitting unit 10A' compact, as compared to the ultraviolet light emitting unit 10A shown in FIG. 5.

Filtering Member

As described above, the inventor found that the wavelength range that does not harm the human cells but is able to deactivate (sterilize) the desired bacteria (objects to be sterilized) is between 190 nm, inclusive, and 237 nm, inclusive.

The center wavelength of the KrCl excimer lamp is between 200 nm and 300 nm, and the center wavelength of the KrBr excimer lamp is also between 200 nm and 300 nm. Thus, most of the light emitted from the KrCl excimer lamp and the KrBr excimer lamp has the wavelength within the wavelength range between 190 nm and 237 nm. However, each of the KrCl excimer lamp and the KrBr excimer lamp emits ultraviolet light having the wavelength outside the wavelength range from 190 nm to 237 nm. This embodiment, therefore, utilizes the filtering member 40 to hinder (block) the transmission of the ultraviolet light having the wavelength outside the wavelength range from 190 nm to 237 nm.

Figure 9:
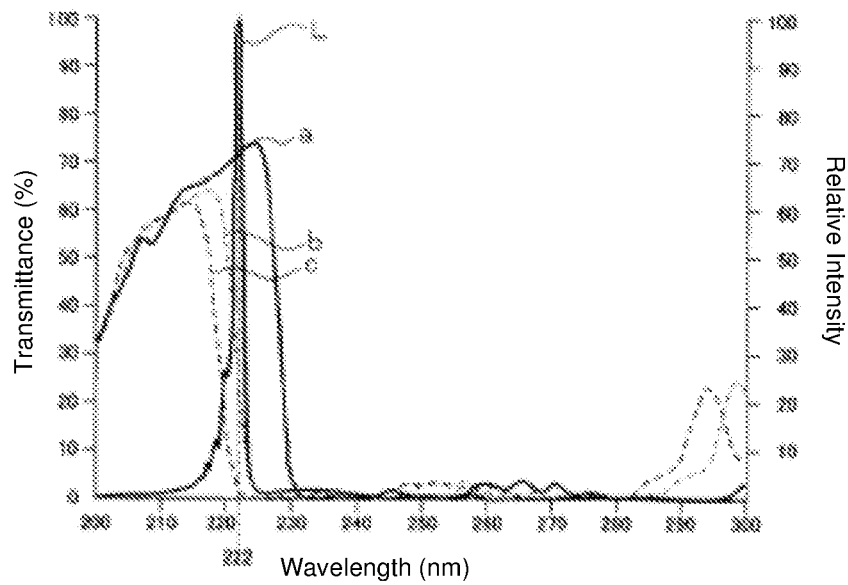
FIG. 9 shows a spectral distribution of light transmittance of a filtering member for comparison.

FIG. 9 shows a spectral distribution of light transmittance of an optical filter for comparison, together with an optical spectrum of the KrCl excimer lamp. This optical filter was prepared to block the transmission of the light having the wavelength outside the wavelength range from 190 nm to 230 nm. Conventionally, it is considered that the wavelength range from 190 nm to 230 nm does not harm the human cells, and deactivates (sterilizes) the desired bacteria (objects to be sterilized).

The optical filter has a dielectric multi-layer film, in which $SiO_2$ layers and $Al_2O_3$ layers are alternately laminated on each of two opposite surfaces of a substrate. The substrate is made from synthetic quartz glass. The number of the $SiO_2$ layers and $Al_2O_3$ layers in the dielectric multi-layer film is 230. The total thickness of the dielectric multi-layer film is over 10 µm.

In FIG. 9, the curve a indicates the spectral distribution of light transmittance when the light is incident to the optical filter at the incident angle of zero, the curve b indicates the spectral distribution of light transmittance when the light is incident to the optical filter at the incident angle of 25 degrees, and the curve c indicates the spectral distribution of light transmittance when the light is incident to the optical filter at the incident angle of 30 degrees. The curve L indicates the optical spectrum of the KrCl excimer lamp.

It is clear from FIG. 9 that the light transmittance of the ultraviolet light at the wavelength of 222 nm (peak wavelength of the light emitted from the KrCl excimer lamp) is about 70% when the incident angle is zero degree, about 50% when the incident angle is 25 degrees, and several % when the incident angle is 30 degrees. Thus, the optical filter prepared for comparison has different transmittances that depend on the incident angle, i.e., the optical filter has the incident-angle dependency.

Therefore, when the target microorganisms (microorganisms to be sterilized) are irradiated with the light emitted from the KrCl excimer lamp through the optical filter of FIG. 9, it is not possible to efficiently use the light that is incident to the optical filter at the incident angle over 25 degrees. In short, the light emitted from the light source cannot be used at a high efficiency. Also, because the light having a large incident angle is blocked or attenuated by the optical filter, the light passing through the optical filter has a reduced diffusion angle. Accordingly, it is difficult to obtain a large effective irradiation area at the sterilization target (object to be sterilized).

Figure 10:
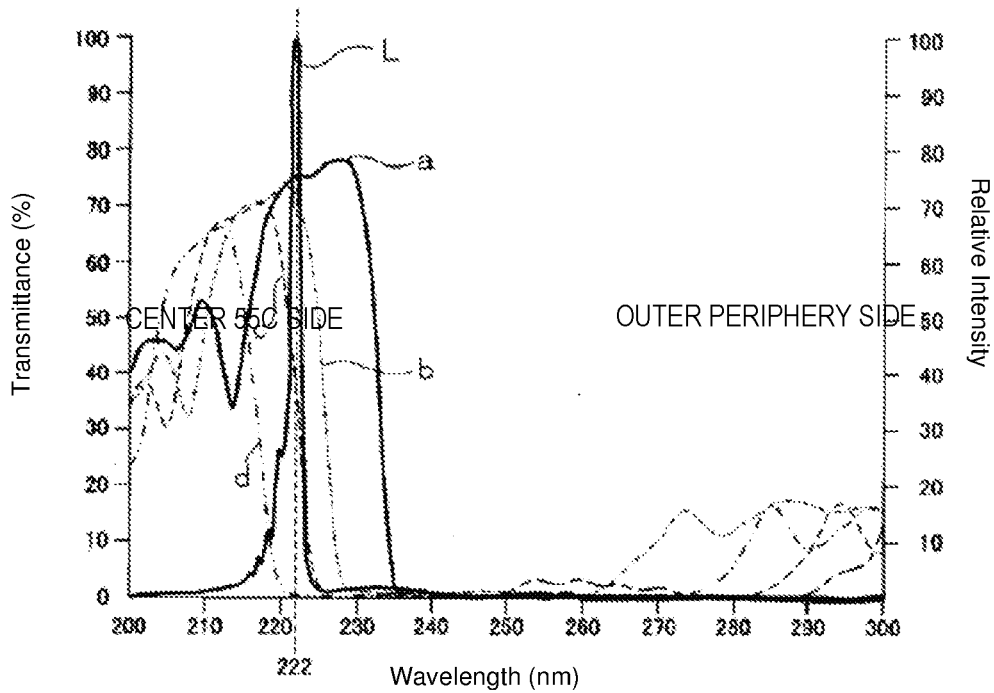
FIG. 10 shows a spectral distribution of light transmittance of a filtering member according to the embodiment of the present invention.

FIG. 10 shows a spectral distribution of light transmittance of the filtering member 40 of this embodiment, together with the optical spectrum of the KrCl excimer lamp. The filtering member (optical filter) 40 was prepared to block the transmission of the light having the wavelength outside the wavelength range from 190 nm to 237 nm.

The optical filter 40 has a dielectric multi-layer film, in which $SiO_2$ layers and $Al_2O_3$ layers are alternately laminated on each of two opposite surfaces of a substrate. The substrate is made from synthetic quartz glass. The number of the $SiO_2$ layers and $Al_2O_3$ layers in the dielectric multi-layer film is 230. The total thickness of the dielectric multi-layer film is over 10 µm.

In FIG. 10, the curve a indicates the spectral distribution of light transmittance when the light is incident to the optical filter 40 at the incident angle of zero, the curve b indicates the spectral distribution of light transmittance when the light is incident to the optical filter 40 at the incident angle of 25 degrees, the curve c indicates the spectral distribution of light transmittance when the light is incident to the optical filter 40 at the incident angle of 30 degrees, and the curve d indicates the spectral distribution of light transmittance when the light is incident to the optical filter 40 at the incident angle of 40 degrees. The curve L indicates the optical spectrum of the KrCl excimer lamp.

It is clear from FIG. 10 that the light transmittance of the ultraviolet light at the wavelength of 222 nm is about 75% when the incident angle is zero degree, over 50% when the incident angle is 25 degrees, over 40% when the incident angle is 30 degrees, and several % when the incident angle is 40 degrees.

When the optical filter 40 having the optical characteristics shown in FIG. 10 is used, and the target microorganisms are irradiated with the light emitted from the KrCl excimer lamp through the optical filter 40, the desired result will be obtained if the incident angle of the light to the optical filter 40 is equal to or smaller than 30 degrees.

Thus, when the optical filter 40 having the optical characteristics shown in FIG. 10 is employed, it is possible to efficiently (effectively) use the light having a large (larger) incident angle, as compared to the optical filter having the optical characteristics shown in FIG. 9, even if the optical filter of FIG. 10 and the optical filter of FIG. 9 are made from the same material.

Figure 11:
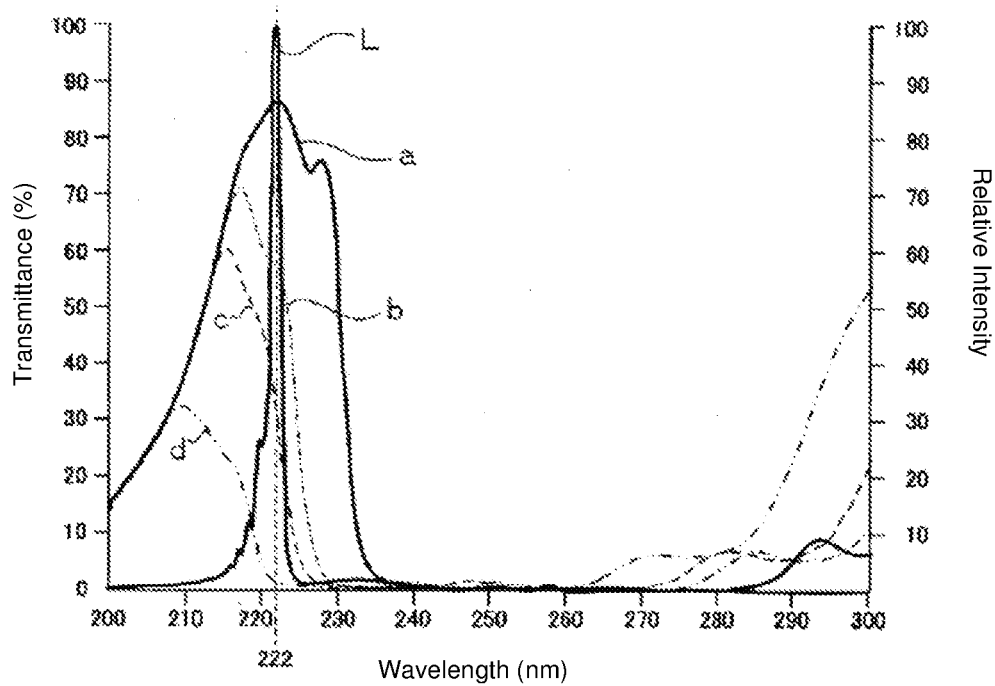
FIG. 11 shows a spectral distribution of light transmittance of a filtering element according to the embodiment of the present invention.

FIG. 11 shows a spectral distribution of light transmittance of another filtering member 40 of this embodiment, together with the optical spectrum of the KrCl excimer lamp. The filtering member (optical filter) 40 was prepared to block the transmission of the light having the wavelength outside the wavelength range from 190 nm to 237 nm.

The optical filter 40 of FIG. 11 has a dielectric multi-layer film, in which $HfO_2$ layers and $SiO_2$ layers are alternately laminated on one of two opposite surfaces of a substrate. The substrate is made from synthetic quartz glass. The thickness of the $HfO_2$ layers in the dielectric multi-layer film is about 240 nm, and the thickness of the $SiO_2$ layers is about 1460 nm. The number of the $HfO_2$ layers and $SiO_2$ layers in the dielectric multi-layer film is 33. The total thickness of the $HfO_2$ layers and the $SiO_2$ layers is 1700 nm. The opposite surface of the substrate is coated with an AR coating, which includes $HfO_2$ layers and $SiO_2$ layers.

In FIG. 11, the curve a indicates the spectral distribution of light transmittance when the light is incident to the optical filter 40 at the incident angle of zero, the curve b indicates the spectral distribution of light transmittance when the light is incident to the optical filter 40 at the incident angle of 25 degrees, the curve c indicates the spectral distribution of light transmittance when the light is incident to the optical filter 40 at the incident angle of 30 degrees, and the curve d indicates the spectral distribution of light transmittance when the light is incident to the optical filter 40 at the incident angle of 40 degrees. The curve L indicates the optical spectrum of the KrCl excimer lamp.

It is clear from FIG. 11 that the light transmittance of the ultraviolet light at the wavelength of 222 nm is about 85% when the incident angle is zero degree, over 50% when the incident angle is 25 degrees, about 35% when the incident angle is 30 degrees, and several % when the incident angle is 40 degrees.

When the optical filter 40 having the optical characteristics shown in FIG. 11 is used, and the target microorganisms are irradiated with the light emitted from the KrCl excimer lamp through the optical filter 40, the desired result will be obtained if the incident angle of the light to the optical filter 40 is equal to or smaller than 30 degrees.

Thus, when the optical filter 40 having the optical characteristics shown in FIG. 11 is employed, it is possible to efficiently (effectively) use the light having a large (larger) incident angle, as compared to the optical filter having the optical characteristics shown in FIG. 9.

As described above, the optical filters 40 having the optical characteristics shown in FIGS. 10 and 11 transmit the light having a large (larger) incident angle. Thus, the optical filters 40 can emit the light having a large (larger) diffusion angle. As a result, it is possible to obtain a large effective irradiation area if the optical filters 40 are used. Thus, it is easy to adjust the ultraviolet light emitting units 10A and 10B such that the ultraviolet light emitted from the ultraviolet light emitting units 10A and 10B illuminates the entire side wall 105A, the entire side wall 105B, and the entire bottom 103 of the hollow portion 104.

When the filtering member 40 is the optical filter that has the dielectric multi-layer film, which is made from the $HfO_2$ layers and the $SiO_2$ layers, it is possible to reduce the total number of the layers, as compared to the optical filter that has the dielectric multi-layer film, which is made from the $SiO_2$ layers and the $Al_2O_3$. As the total number of the layers decreases, it is possible to increase the transmittance of the ultraviolet light when the incident angle is zero degree. Reducing the total number of the layers also contributes to a cost reduction.

Modifications

Although the dry sterilization device 100 of the above-described embodiment includes the two ultraviolet light emitting units 10A and 10B, one of the ultraviolet light emitting units 10A and 10B may be replaced with a reflection mirror.

FIG. 12 is a side view of a dry sterilizing device 100A that includes the ultraviolet light emitting unit 10A and a reflection mirror 110. The ultraviolet light emitting unit 10B is replaced with the reflection mirror 110. FIG. 13 is similar to FIG. 4 and illustrates a cross-sectional view of the dry sterilizing device 100A shown in FIG. 12

In the dry sterilizing device 100A, the reflection mirror 110 is fixed on the side wall 105B such that the ultraviolet light emitted from the ultraviolet light emitting unit 10A disposed on the opposite side wall 105A is reflected by the reflection mirror 110. The reflection mirror 110 is fixed at a position that allows the ultraviolet light reflected by the reflection mirror 110 to illuminate the entire side wall 105A of the hollow portion 104 and part of the bottom 103. Thus, the ultraviolet light emitting unit 10A and the reflection mirror 110 are arranged such that the entire side wall 105A, the entire side wall 105B and the entire bottom 103 of the hollow portion 104 are irradiated with the ultraviolet light emitted from the ultraviolet light emitting unit 10A and the ultraviolet light reflected by the reflection mirror 110.

As shown in FIG. 13, the power supply unit 130 supplies an electric power to the ultraviolet light emitting unit 10A, the sensors 108, the heaters 113, and the drive motors (not shown) of the air blowers 112. Unlike the configuration shown in FIG. 4, the power source 130 does not supply the electric power to the ultraviolet light emitting unit 10B. The controller 135 controls the power supply unit 130. Unlike the configuration shown in FIG. 4, the controller 135 does not control the power supply unit 130 for the ultraviolet light emitting unit 10B.

Accordingly, the dry sterilizing device 100A shown in FIGS. 12 and 13 can save the electric power, as compared to the dry sterilizing device 100 shown in FIGS. 2 and 4.

The Operation Modes of the Dry Sterilizing Device

The operation modes of the dry sterilizing device 100 will be described below.

First Operation Mode

Figure 14:
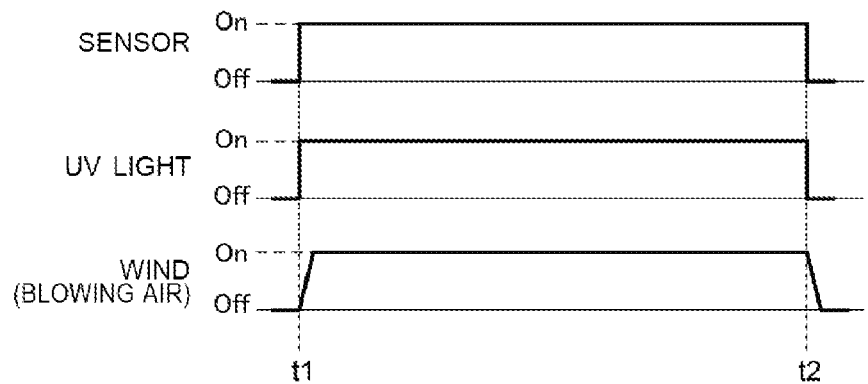
FIG. 14 is a timing chart to describe a first operation mode of the dry sterilizing device.

FIG. 14 is a timing chart to describe a first operation mode of the dry sterilizing device 100.

When the sensors 108 detect the presence of the hands and fingers in the hollow portion 104, the sensors 108 send the detection signals to the controller 135. Upon receiving the detection signals, the controller 135 controls the power supply unit 130 to start supplying the electric power to the ultraviolet light emitting units 10A and 10B and the drive motors of the blower fans 112.

Referring to FIG. 14, when the detection signals of the sensors 108 become On at the time t1, the ultraviolet light emitting units 10A and 10B emit the ultraviolet light into the hollow portion 104. The ultraviolet light emitted from the ultraviolet light emitting units 10A and 10B includes at least part of the ultraviolet light having the wavelength between 190 nm and 230 nm and at least part of the ultraviolet light having the wavelength between 230 nm and 237 nm, but does not include the ultraviolet light having the wavelength outside the wavelength range between 190 nm and 237 nm. At the time t1, the drive motors of the blower fans are activated, and the high-speed warm (or hot) air 107 blows from the air nozzles 106.

Subsequently, when the hands and fingers are lifted from the hollow portion 104, the sensors 108 no longer detect the hands and fingers. Thus, the sensors 108 stop sending the detection signals. Then, the controller 135 controls the power supply unit 130 to stop feeding the electricity to the ultraviolet light emitting units 10A and 10B and the drive motors of the blower fans 112. Therefore, when the detection signals of the sensors 108 become Off (at the time t2), the ultraviolet light emission to the hollow portion 104 stops, and the blowing of the high-speed warm air 107 to the hollow portion 104 from the air nozzles 106 also stops. In this specification, the detection signals being Off means that the sensors 108 do not detect the hands and fingers in the hollow portion 104 and generate no detection signal. The detection signals being On means that the sensors 108 detect the hands and fingers in the hollow portion 104 and generate the detection signals that indicate the presence of the hands and fingers.

In the first operation mode, therefore, the dry sterilizing device 100 sends the air to the hands and fingers and irradiate the hands and fingers with the ultraviolet light while the hands and fingers are present in the hollow portion 104. As such, the dry sterilizing device 100 can appropriately dry and sterilize the hands and fingers.

Second Operation Mode

Figure 15:
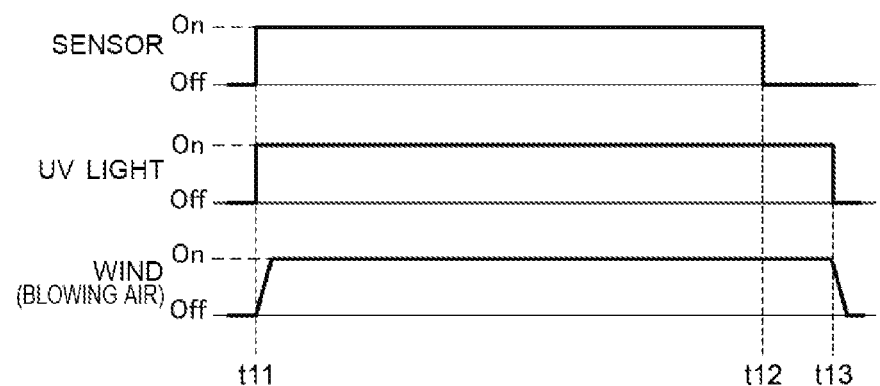
FIG. 15 is a timing chart to describe a second operation mode of the dry sterilizing device.

FIG. 15 is a timing chart to describe a second operation mode of the dry sterilizing device 100. The operation at the time t11 in the second operation mode is the same as the operation at the time t1 in the first operation mode.

In the second operation mode, when the detection signals of the sensors 108 become Off at the time t12, the controller 135 controls the power supply unit 130 to keep feeding the electricity to the ultraviolet light emitting units 10A and 10B and the drive motors of the blower fans 112 for a predetermined period of time. When the predetermined period of time elapses from the time t12 (i.e., when the time t13 is reached), the controller 135 controls the power supply unit 130 to stop feeding the electricity to the ultraviolet light emitting units 10A and 10B and the drive motors of the blower fans 112

In this manner, even after the detection signals of the sensors 108 become Off, the ultraviolet light emission to the hollow portion 104 continues for the predetermined period of time, and the blowing of the high-speed warm air 107 to the hollow portion 104 from the air nozzles 106 also continues for the predetermined period of time. Because the ultraviolet light emission to the hollow portion 104 continues even after the hands and fingers leave the hollow portion 104, it is possible to deactivate the bacteria remaining in the hollow portion 104. Because the high-speed warm air 107 keeps blowing to the hollow portion 104 from the air nozzles 106 even after the hands and fingers leave the hollow portion 104, it is possible to facilitate and urge (accelerate) the movement of the water droplets to the bottom 103 from the side walls 105A and 105B of the hollow portion 104.

It should be noted that the ultraviolet light emission to the hollow portion 104 may only continue for the predetermined period of time after the detection signals of the sensors 108 become Off.

Third Operation Mode

Figure 16:
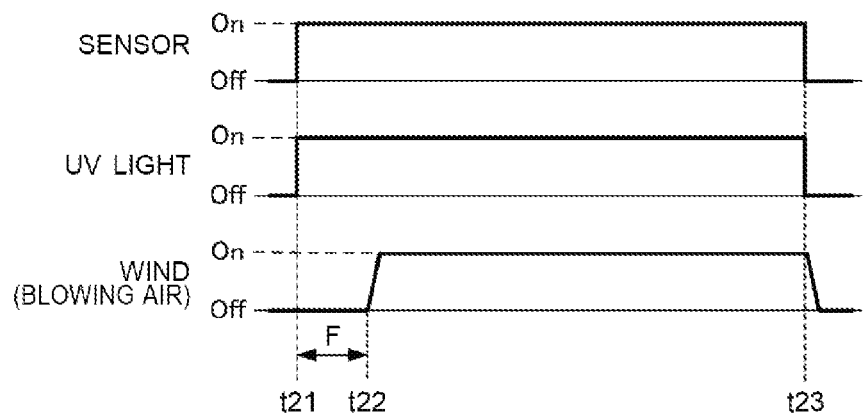
FIG. 16 is a timing chart to describe a third operation mode of the dry sterilizing device.

FIG. 16 is a timing chart to describe a third operation mode of the dry sterilizing device 100.

In the third operation mode, when the sensors 108 detect the presence of the hands and fingers in the hollow portion 104, and send the detection signals to the controller 135, the controller 135 receives the detection signals and controls the power supply unit 130 to start supplying the electric power to the ultraviolet light emitting units 10A and 10B. After the elapse of a predetermined period of time F, the controller 135 controls the power supply unit 130 to start supplying the electric power to the drive motors of the blower fans 112.

Thus, when the detection signals of the sensors 108 become On at the time t21, the ultraviolet light emission to the hollow portion 104 from the ultraviolet light emitting units 10A and 10B starts. At the time t22 (i.e., after the predetermined period of time F elapses from the time t21), the blowing of the high-speed warm air 107 to the hollow portion 104 from the air nozzles 106 starts.

When the hands and fingers leave the hollow portion 104, the detection signals of the sensors 108 become Off at the time t23. Then, the controller 135 controls the power supply unit 130 to stop supplying the electricity to the ultraviolet light emitting units 10A and 10B and the drive motors of the blower fans 112. As a result, the ultraviolet light emitting units 10A and 10B stop emitting the ultraviolet light to the hollow portion 104, and the air nozzles 106 stop sending the warm air 107 to the hollow portion 104.

In this manner, after starting the emission of the ultraviolet light, the high temperature air 107 blows from the air nozzles 106 upon the elapse of the predetermined delay time F. Thus, the sterilization (deactivation) of the bacteria on the hands and fingers is carried out firstly, and then the removal of the water droplets from the hands and fingers is carried out by the high-speed warm air 107. Therefore, it is possible to significantly reduce an amount of bacteria contained in the water droplets flying (water droplets being carried by the warm air 107) from the hands and fingers toward the side walls 105A and 105B and the bottom 103 and toward the atmosphere around the sterilizing device 100.

Fourth Operation Mode

Figure 17:
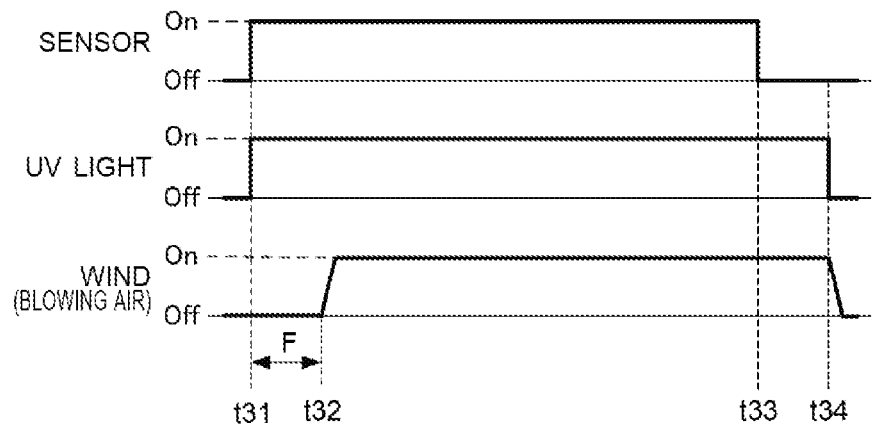
FIG. 17 is a timing chart to describe a fourth operation mode of the dry sterilizing device.

FIG. 17 is a timing chart to describe a fourth operation mode of the dry sterilizing device 100. The operations at the time t31 and the time t32 in the fourth operation mode are the same as the operations at the time t21 and the time t22 in the third operation mode, respectively.

In the fourth operation mode, when the detection signals of the sensors 108 become Off at the time t33, the controller 135 controls the power supply unit 130 to keep feeding the electricity to the ultraviolet light emitting units 10A and 10B and the drive motors of the blower fans 112 for a predetermined period of time. When the predetermined period of time elapses from the time t33 (i.e., when the time t34 is reached), the controller 135 controls the power supply unit 130 to stop feeding the electricity to the ultraviolet light emitting units 10A and 10B and the drive motors of the blower fans 112.

Thus, even after the detection signals of the sensors 108 become Off, the ultraviolet light emission to the hollow portion 104 continues for the predetermined period of time, and the blowing of the high-speed warm air 107 to the hollow portion 104 from the air nozzles 106 also continues for the predetermined period of time. Because the ultraviolet light emission to the hollow portion 104 continues even after the hands and fingers leave the hollow portion 104, it is possible to deactivate the bacteria remaining in the hollow portion 104. Because the high-speed warm air 107 keeps blowing to the hollow portion 104 from the air nozzles 106 even after the hands and fingers leave the hollow portion 104, it is possible to facilitate and accelerate the movement of the water droplets to the bottom 103 from the side walls 105A and 105B of the hollow portion 104.

In the fourth operation mode, the sterilization (deactivation) of the bacteria on the user's hands and fingers is carried out by the ultraviolet light emitted from the ultraviolet light emitting units 10A and 10B prior to the blowing of the high-speed warm air 107, and therefore the blowing of the high-speed air 107 may only continue for a predetermined period of time after the detection signals of the sensors 108 become Off.

Fifth Operation Mode

Figure 18:
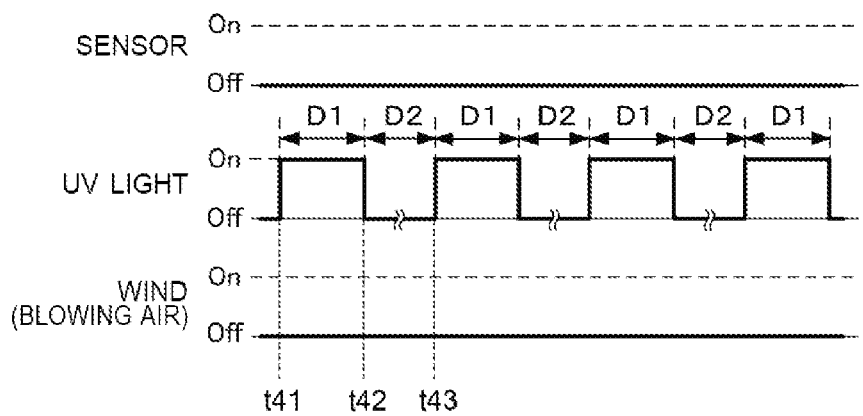
FIG. 18 is a timing chart to describe a fifth operation mode of the dry sterilizing device.

FIG. 18 is a timing chart to describe a fifth operation mode of the dry sterilizing device 100.

In the fifth operation mode, the controller 135 controls the power supply unit 130 to supply the electricity to the ultraviolet light emitting units 10A and 10B at predetermined intervals while the sensors 108 do not detect the presence of the hands and fingers in the hollow portion 104. Specifically, the controller 135 keeps supplying the electricity during the predetermined period of time D1 and stops supplying the electricity during the predetermined period of time D2. The controller 135 restarts supplying the electricity upon the elapse of the predetermined period of time D2, and keeps supplying the electricity during the predetermined period of time D1. The controller 135 repeats such electricity feeding intermittently (at the predetermined intervals).

Accordingly, when the detection signals of the sensors 108 become Off at the time t41, the ultraviolet light is emitted into the hollow portion 104, and this light emission continues for the predetermined period of time D1. When the predetermined period of time D1 elapses from the time t41 (i.e., when the time t42 is reached), the emission of the ultraviolet light stops. When the predetermined period of time D2 elapses (i.e., when the time t43 is reached), the ultraviolet light is again emitted into the hollow portion 104. These operations are repeated while the detection signals of the sensors 108 are Off. Thus, even when the detection signals of the sensors 108 are Off, the ultraviolet light is periodically emitted into the hollow portion 104. The bacteria present in the hollow portion 104 (space for drying and sterilization) are periodically sterilized while no hands and fingers are present in the hollow portion 104. Thus, it is possible to suppress the growth and increase of the bacteria in the hollow portion 104.

If the controller 135 has a timer, the periodical emission of the ultraviolet light may be regulated (governed) by a flicker action of the timer in the controller 135. When the timer counts the predetermined period of time D1 (or D2) and the sensors 108 detect the presence of the hands and fingers in the hollow portion 104, then the flicker action of the timer may stop and the priority may be given to the control with the sensors 108. The control to be carried out with the sensors 108 may be the control shown in any one of FIGS. 14 to 17.

In the foregoing, the ultraviolet light emitting units 10A and 10B are repeatedly (periodically) activated during the activation period D1 and deactivated during the deactivation period D2. It should be noted, however, that if the ultraviolet light emitting units 10A and 10B are activated and emit the ultraviolet light at least for a certain period of time while the detection signals of the sensors 108 are Off, then it is possible to obtain the advantage of the fifth operation mode (i.e., the bacteria in the hollow portion 104 are sterilized while no hands and fingers are present in the hollow portion 104, and therefore it is possible to suppress the growth and increase of the bacteria in the hollow portion 104) to a certain extent.

Sixth Operation Mode

Figure 19:
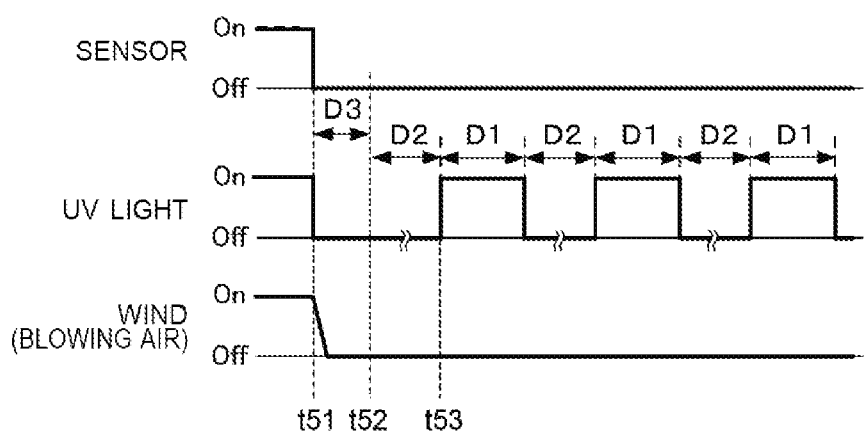
FIG. 19 is a timing chart to describe a sixth operation mode of the dry sterilizing device.

FIG. 19 is a timing chart to describe a sixth operation mode of the dry sterilizing device 100.

In the sixth operation mode, when the detection signals of the sensors 108 become Off at the time t51, the controller 135 controls the power supply unit 130 to stop feeding the electricity to the ultraviolet light emitting units 10A and 10B and the drive motors of the blower fans 112. Then, the timer in the controller 135 stops the flicker action for a predetermined period of time D3. When the predetermined period of time D3 elapses (i.e., when the time t52 is reached), the timer resumes the flicker action. Then, the controller 135 controls the power supply unit 130 to periodically supply the electricity to the ultraviolet units 10A and 10B (at the predetermined intervals). The operation after the time t53 in the sixth operation mode is the same as the operation after the time t41 in the fifth operation mode. The predetermined period of time D3 is set to a value during which no one will presumably use the sterilizing device 100 after the current user.

Thus, when the predetermined period of time D3 elapses after the detection signals of the sensors 108 become Off, the ultraviolet light is periodically emitted into the hollow portion 104. In other words, when it is determined that a next user is not coming, the bacteria in the hollow portion 104 are periodically sterilized.

As described above, the dry sterilizing device 100 of this embodiment sends the warm current of air 107 to the object (e.g., hands and fingers) present in the hollow portion 104 of the housing 101 and emits (directs) the ultraviolet light to the object from the ultraviolet light emitting units 10A and 10B to dry and sterilize the object.

Most of the water droplets, which are removed from the hands and fingers by the warm air 107, are caught by the inner walls (bottom 103 and the side walls 105A and 105B) of the hollow portion 104 of the dry sterilizing device 100, but some of the water droplets fly to the environment. Because the dry sterilizing device 100 can sterilize the bacteria on the hands and fingers with the ultraviolet light while removing the water droplets from the hands and fingers, it is possible to suppress the diffusion of the bacteria in the hollow portion 104 and to the environment.

The dry sterilizing device 100 emits to the user's hands and fingers at least part of the ultraviolet light having the wavelength between 190 nm and 230 nm and at least part of the ultraviolet light having the wavelength between 230 nm and 237 nm. Therefore, the dry sterilizing device 100 can deactivate (e.g., sterilize) the target, i.e., bacteria, present in a target area of a human body while substantially avoiding a harmful effect to the human cells. As such, the dry sterilizing device 100 can dry and sterilize the user's hands and fingers without exerting an adverse influence on the human body.

Specifically, when the light emitted from the light source enters the sterilizing device 100 at the incident angle of zero degree, the filtering device (optical filter) 40 of the sterilizing device 100 transmits at least part of the ultraviolet light having the wavelength between 190 nm and 230 nm and at least part of the ultraviolet light having the wavelength between 230 nm and 237 nm while blocking the transmission of the ultraviolet light having the wavelength outside the wavelength range between 190 nm and 237 nm. The sterilizing device 100 directs the desired components of the light, which is emitted from the light source, to the interior of the hollow portion 104 via the filtering member 40.

Because the filtering member 40 is utilized in the above-described manner, it is possible to appropriately extract from the light source the ultraviolet light components having the wavelength range that is not harmful to the human body.

Also, because the filtering member 40 having the above-described optical characteristics is employed, it is possible to use the light emitted from the light source at a high efficiency, and contribute to the energy saving of the dry sterilizing device 100. Furthermore, because the filtering member 40 having the above-described optical characteristics can transmit the light having a large incident angle, it is possible to emit the light having a large diffusion angle from the filtering member 40 and obtain a large effective irradiation area.

The dry sterilizing device 100 emits the ultraviolet light to the entire inner wall (side walls 105A and 105B and the bottom 103) of the hollow portion 104, i.e., the target space for the drying and sterilization, and therefore it is possible to deactivate the bacteria even if the bacteria adhere to the inner wall of the hollow portion 104. Accordingly, it is possible to prevent or suppress the growth and increase of the bacteria in the hollow portion 104. It is also possible to prevent the bacteria from flying to the environment with the wind.

In particular, the water droplets removed from the hands and fingers by the warm air 107 move to the bottom 103 of the hollow portion 104, and therefore the bacteria are likely to grow and increase at the bottom 103. In this embodiment, the ultraviolet light emitting units 10A and 10B are arranged such that the ultraviolet light emitted from these units 10A and 10B reach the bottom 103 of the hollow portion 104. Thus, it is possible to efficiently and effectively suppress the growth and increase of the bacteria.

If the inner wall of the hollow portion 104 of the dry sterilizing device 100 is wet, bacteria flying in the atmosphere may adhere to the inner wall of the hollow portion 104 and grow (increase) on the inner wall of the hollow portion 104. If it occurs, the bacteria may fly to the environment from the hollow portion 104 with the warm wind 107 blowing from the air nozzles 106 when a next user uses the dry sterilizing device 100.

The dry sterilizing device 100 of this embodiment includes the controller 135 to appropriately control the timing of sending the high-speed warm wind 107 toward the hands and fingers, and the timing of emitting the ultraviolet light (UV light) to the hands and fingers. Thus, it is significantly reduce or prevent the bacteria and other substances from flying in the hollow portion 104 and to the environment (atmosphere around the dry sterilizing device 100).

For example, when the controller 135 receives the detection signals from the sensors 108, which indicate that the user's hands and fingers have left the hollow portion 104, the controller 135 can continue the air blowing and the ultraviolet light emission for a predetermined period of time. This can sterilize the bacteria remaining in the hollow portion 104 and remove the water droplets and moisture remaining in the hollow portion 104. Thus, the growth and increase of the bacteria in the hollow portion 104 is prevented.

When the controller 135 detects the presence of the user's hands and fingers in the hollow portion 104, the controller 135 may start the emission of the ultraviolet light, and when a predetermined period of time elapses after the start of the ultraviolet light emission, the controller 135 may start the blowing of the warm air. In such a case, the sterilization of the bacteria on the hands and fingers is firstly carried out, and then the removal of the water droplets and moisture adhering onto the hands and fingers is carried out by the warm wind 107. Thus, it is possible to reduce an amount of bacteria included in the water droplets flying upon blowing of the warm air 107, and suppress the diffusion of the bacteria in the hollow portion 104 and to the surrounding atmosphere.

Also, the controller 135 can cause the ultraviolet light emitting units 10A and 10B to emit the ultraviolet light into the hollow portion 104 for at least a predetermined period time while the controller 135 is detecting the absence of the user's hands and fingers in the hollow portion 104. In such a case, it is possible to appropriately sterilize the bacteria remaining in the hollow portion 104 and appropriately suppress the growth and increase of the bacteria in the hollow portion 104. If the emission of the ultraviolet light is periodically carried out while the controller 135 is detecting the absence of the user's hands and fingers in the hollow portion 104, it is possible to sterilize the bacteria remaining in the hollow portion 104 in a more appropriate manner.

As described above, the dry sterilizing device 100 of this embodiment can sterilize the bacteria without causing the ultraviolet light, which is used for sterilization of hands and fingers, to exert a harmful effect to the human body. The sterilizing device 100 can sterilize the bacteria remaining in the hollow portion 104 (i.e., the space for drying and sterilization), and suppress the growth and increase of bacteria in the hollow portion 104.

Modifications

In the above-described embodiment, the dry sterilizing device 100 dries and sterilizes the hands and fingers of a user. In other words, the target (object) to be dried and sterilized is the user's hands and fingers. It should be noted that the target to be dried and sterilized is not limited to the hands and fingers. For example, the medical equipment, the barber's scissors and other devices which should be hygienic may also be the object to be dried and sterilized. A user may hold the object and place the object in the hollow portion 104 to dry and sterilize the object. The hands and fingers may be irradiated with the ultraviolet light when the user places the object in the hollow portion 104. Thus, it is desired that the ultraviolet light used for sterilization does not exert a harmful effect to a human body. The dry sterilizing device 100 is advantageously used to dry and sterilize an object including part of a human body.

While certain embodiments have been described, these embodiments have been presented by way of example only, and are not intended to limit the scope of the present invention. The novel apparatuses and methods thereof described herein may be embodied in a variety of other forms; furthermore, various omissions, substitutions and changes in the form of the apparatuses and methods thereof described herein may be made without departing from the gist of the present invention. The accompanying claims and their equivalents are intended to cover such forms or modifications as would fall within the scope and gist of the present invention.

What is claimed is:

1. A sterilizing device comprising:
   a housing having an opening in at least one direction thereof, and also having a hollow portion configured to allow insertion of an object including part of a human body from the opening into the hollow portion;
   at least one air blower unit configured to make a flow of air toward an interior of the hollow portion;
   at least one ultraviolet light emitting unit configured to emit ultraviolet light toward the interior of the hollow portion, the ultraviolet light emitted from the at least one ultraviolet light emitting unit including at least part of a wavelength between 190 nm and 230 nm and at least part of a wavelength between 230 nm and 237 nm, but not including a wavelength below 190 nm and beyond 237 nm;
   at least one sensor unit configured to detect presence of the object in the hollow portion;
   a power supply unit configured to supply electricity to the at least one air blower unit, the at least one ultraviolet light emitting unit and the at least one sensor unit; and
   a controller unit configured to control the power supply unit based on a detection result of the at least one sensor unit, in order to control operations of the at least one air blower unit and the at least one ultraviolet light emitting unit,
   wherein the controller unit causes the power supply unit to supply the electricity to the at least one ultraviolet light emitting unit thereby causing the at least one ultraviolet light emitting unit to emit the ultraviolet light when the at least one sensor unit detects the presence of the object in the hollow portion, and the controller unit causes the power supply unit to supply the electricity to the at least one air blower unit thereby causing the at least one air blower unit to produce the flow of air after a predetermined period of time elapses upon supplying the electricity to the at least one ultraviolet light emitting unit.

2. The sterilizing device according to claim 1, wherein the at least one ultraviolet light emitting unit includes:
   a light source to emit light including ultraviolet light having a wavelength between 190 nm and 237 nm; and
   a filtering member through which the light emitted from the light source passes, such that the light having passed through the filtering member proceeds toward the interior of the hollow portion, and
   the filtering member being configured to transmit at least part of the ultraviolet light having the wavelength between 190 nm and 230 nm and at least part of the ultraviolet light having the wavelength between 230 nm and 237 nm and to block transmission of the ultraviolet light having the wavelength outside a wavelength range between 190 nm and 237 nm when the light emitted from the light source enters the filtering member at an incident angle of zero degree.

3. The sterilizing device according to claim 2, wherein the light source is a KrCl excimer lamp or a KrBr excimer lamp.

4. The sterilizing device according to claim 3, wherein a lighting tube of the KrCl excimer lamp or the KrBr excimer lamp is made from a dielectric substance, and is a rectangular parallelepiped hollow tube having a rectangular cross-sectional shape.

5. The sterilizing device according to claim 2, wherein the at least one ultraviolet light emitting unit includes a reflection member configured to reflect the light emitted from the light source toward the interior of the hollow portion through the filtering member.

6. The sterilizing device according to claim 2, wherein the filtering member has a dielectric multi-layer film made from at least one $SiO_2$ layer and at least one $Al_2O_3$ layer.

7. The sterilizing device according to claim 2, wherein the filtering member has a dielectric multi-layer film made from at least one $HfO_2$ layer and at least one $SiO_2$ layer.

8. The sterilizing device according to claim 1, wherein the at least one ultraviolet light emitting unit emits the ultraviolet light such that the ultraviolet light reaches at least part of an inner wall of the hollow portion.

9. The sterilizing device according to claim 1, wherein the opening is provided at an upper portion of the hollow portion, and the hollow portion has at least two side walls and a bottom portion opposite to the opening, the at least two side walls including two side walls that face each other and
the at least one ultraviolet light emitting unit emits the ultraviolet light such that the ultraviolet light reaches the two side walls and the bottom portion of the hollow portion.

10. The sterilizing device according to claim 1, wherein the hollow portion has two side walls that face each other, and the at least one ultraviolet light emitting unit includes two ultraviolet light emitting units disposed on the two side walls, respectively.

11. The sterilizing device according to claim 1, wherein the at least one ultraviolet light emitting unit includes a single ultraviolet light emitting unit, the hollow portion has two facing side walls, the single ultraviolet light emitting unit is disposed on one of the two side walls, and a reflection mirror is disposed on the other of the two side walls such that the reflection mirror reflects part of the ultraviolet light emitted from the single ultraviolet light emitting unit toward the interior of the hollow portion.

12. The sterilizing device according to claim 1, wherein the controller unit controls the power supply unit to deactivate the at least one air blower unit and the at least one ultraviolet light emitting unit after a predetermined period of time elapses upon detecting absence of the object in the hollow portion by the at least one sensor unit.

13. The sterilizing device according to claim 1, wherein the controller unit controls the power supply unit for a predetermined period of time to activate the at least one ultraviolet light emitting unit while the at least one sensor unit is not detecting the presence of the object in the hollow portion.

14. The sterilizing device according to claim 13, wherein the controller unit intermittently causes the power supply unit to supply the electricity to the at least one ultraviolet light emitting unit for a predetermined number of times while the at least one sensor unit is not detecting the presence of the object in the hollow portion.

15. The sterilizing device according to claim 13, wherein the controller unit keeps the at least one ultraviolet light emitting unit deactivated if the at least one sensor unit does not detect the presence of the object in the hollow portion for a predetermined period of time after deactivation of the at least one ultraviolet light emitting unit upon detecting absence of the object in the hollow portion by the at least one sensor unit.

16. A sterilizing device comprising:
a housing having a bottom and two side walls, which face each other, such that the bottom and the two side walls define, in combination, a space having an upper opening to allow insertion of an object including part of a human body from the upper opening into the space;
two air blower units disposed in the two side walls, respectively, such that each of the two air blower units is configured to make a flow of air toward an interior of the space; and
at least one ultraviolet light emitting unit configured to emit ultraviolet light toward the interior of the space,
the ultraviolet light emitted from the at least one ultraviolet light emitting unit including at least part of a wavelength between 190 nm and 230 nm and at least part of a wavelength between 230 nm and 237 nm, but not including a wavelength below 190 nm and beyond 237 nm.

17. The sterilizing device according to claim 16, further including two heating units disposed in the two side walls, respectively, to heat the flow of air.

* * * * *